(12) United States Patent
Brennan et al.

(10) Patent No.: US 7,602,307 B1
(45) Date of Patent: Oct. 13, 2009

(54) PORTABLE MODULAR DETECTION SYSTEM

(75) Inventors: James S. Brennan, Rodeo, CA (US); Anup Singh, Danville, CA (US); Daniel J. Throckmorton, Tracy, CA (US); James F. Stamps, Livermore, CA (US)

(73) Assignee: Sandia Corporation, Livermore, CA (US)

( * ) Notice: Subject to any disclaimer, the term of this patent is extended or adjusted under 35 U.S.C. 154(b) by 269 days.

(21) Appl. No.: 11/559,154

(22) Filed: Nov. 13, 2006

(51) Int. Cl.
*G08B 21/00* (2006.01)
(52) U.S. Cl. .......... 340/686.2; 340/521; 340/576; 340/10.1; 356/338; 356/339; 356/369; 374/120; 374/161
(58) Field of Classification Search .......... 340/686.2, 340/521, 576, 10.1; 356/338, 339, 369; 374/120, 374/161
See application file for complete search history.

(56) References Cited

U.S. PATENT DOCUMENTS

| | | | | |
|---|---|---|---|---|
| 5,515,163 | A | * | 5/1996 | Kupershmidt et al. ....... 356/338 |
| 5,777,314 | A | * | 7/1998 | Roustaei ................. 235/462.42 |
| 6,268,914 | B1 | * | 7/2001 | Wang .......................... 356/365 |
| 6,407,395 | B1 | | 6/2002 | Perov |
| 6,595,685 | B2 | * | 7/2003 | Baba et al. .................. 374/161 |
| 6,998,598 | B2 | | 2/2006 | Horn |

* cited by examiner

*Primary Examiner*—Tai T Nguyen
(74) *Attorney, Agent, or Firm*—Smith, Gambrell & Russell, LLP; Timothy P. Evans

(57) ABSTRACT

Disclosed herein are portable and modular detection devices and systems for detecting electromagnetic radiation, such as fluorescence, from an analyte which comprises at least one optical element removably attached to at least one alignment rail. Also disclosed are modular detection devices and systems having an integrated lock-in amplifier and spatial filter and assay methods using the portable and modular detection devices.

11 Claims, 6 Drawing Sheets

PORTABLE MODULAR DETECTION SYSTEM

ACKNOWLEDGEMENT OF GOVERNMENT SUPPORT

This invention was made by employees of Sandia National Laboratories. The Government has certain rights in the invention.

BACKGROUND OF THE INVENTION

1. Field of the Invention

The present invention is directed to portable and modular detection devices. In particular, the present invention is directed to portable and modular detection devices performing lock-in amplification.

2. Description of the Related Art

Recent advances in miniaturization, and particularly in the field of microelectro-mechanical structures (MEMS), have led to the development of microfluidic devices that are designed, in part, to perform a multitude of chemical and physical processes on a micro-scale. The attraction of these microsystems lies in the fact that miniaturization provides for substantial advantages in terms of cost, speed, the capability for easy automation, reproducibility, rapidity of analysis, and the need for only very small (µl) samples. As a consequence, microsystems in the form of microfluidic devices are becoming increasingly important in such diverse fields as DNA sequencing, immunochromatography, analysis and identification of explosives, chemical and biological warfare agents, and synthesis of chemicals and drugs.

Because only minute amounts of sample are required these microchemical analysis systems are particularly attractive for not only for rapid chemical analysis but also for the ability to analyze accurately a large number of samples in a short period of time. Unfortunately, prior art devices which are purported to be portable (handheld), modular, and reproducibly detect and measure low concentrations of analytes are not truly portable, modular, incapable of detecting and measuring low concentration of analytes, or a combination thereof.

For example, U.S. Pat. No. 6,998,598 discloses a modular optical detector system which asserts picomolar detection limits. In practice, however, the optical detector exhibits low signal to noise and is only useful in the nanomolar range. Further, the optical detector is not completely modular as only a select few components may be replaced by substantially similar components in a substantially similar location as the original component.

Thus, a need exists for portable and modular detection systems that reproducibly detect and measure low concentrations of chemicals conveniently, safely and quickly.

SUMMARY OF THE INVENTION

In some embodiments, the present invention provides a portable and modular detection system and methods for detecting the presence of an analyte by detecting the emitted or reflected electromagnetic radiation, such as fluorescence, from the analyte.

In some embodiments, the portable and modular detection system comprises an electromagnetic radiation source; at least one alignment rail; at least one optical element removably attached to the alignment rail; a photodetector; and a lock-in amplifier. In some embodiments, the electromagnetic radiation source produces a wavelength ranging from infrared to ultraviolet. In some embodiments, the electromagnetic radiation source is a laser, a pulsed laser, or a light emitting diode. In some embodiments, the optical element is a lens, a mirror, a dichroic mirror, an interference filter, a color filter, a pinhole, an aperture, an iris, a diffractive element, a prism, a polarizer, a collection optic, or a wave plate. In some embodiments, the photodetector is a photoresistor, a photovoltaic cell, a photodiode, a photomultiplier tube, a phototube, a phototransistor, or a charge-coupled device. In some embodiments, the portable and modular detection system further comprises a spatial filter which is optionally removably attached to the alignment rail. In some embodiments, the portable and modular detection system further comprises a light baffling, a stage, a display, a data memory storage, a voltage source, or a combination thereof, which are each independently optionally removably attached. In some embodiments, the photodetector, the electromagnetic radiation source, and the lock-in amplifier are each independently optionally removably attached. In some embodiments, the size of the detection system is less than about 4"×2.5"×1".

In some embodiments, the present invention provides a method for assaying electromagnetic radiation emitted or reflected from an analyte in a sample which comprises collecting and collimating any reflected or emitted electromagnetic radiation from the analyte with at least one optical element removably attached to at least one alignment rail, directing the collimated electromagnetic radiation to a photodetector, converting the reflected or emitted electromagnetic radiation to a voltage signal, using phase sensitive detection to provide an amplified voltage signal, and obtaining the amplified signal within a housing capable of being portable.

In some embodiments, the present invention provides a method for assaying electromagnetic radiation emitted or reflected from an analyte in a sample which comprises detecting, measuring, or monitoring any reflected or emitted electromagnetic radiation from the analyte with a portable and modular detection system described herein. In some embodiments, the portable and modular detection system comprises an electromagnetic radiation source; at least one alignment rail; at least one optical element removably attached to the alignment rail; a photodetector; and a lock-in amplifier. In some embodiments, the electromagnetic radiation source produces a wavelength ranging from infrared to ultraviolet. In some embodiments, the electromagnetic radiation source is a laser, a pulsed laser, or a light emitting diode. In some embodiments, the optical element is a lens, a mirror, a dichroic mirror, an interference filter, a color filter, a pinhole, an aperture, an iris, a diffractive element, a prism, a polarizer, a collection optic, or a wave plate. In some embodiments, the photodetector is a photoresistor, a photovoltaic cell, a photodiode, a photomultiplier tube, a phototube, a phototransistor, or a charge-coupled device. In some embodiments, the portable and modular detection system further comprises a spatial filter which is optionally removably attached to the alignment rail. In some embodiments, the portable and modular detection system further comprises a light baffling, a stage, a display, a data memory storage, a voltage source, or a combination thereof, which are each independently optionally removably attached. In some embodiments, the photodetector, the electromagnetic radiation source, and the lock-in amplifier are each independently optionally removably attached. In some embodiments, the size of the detection system is less than about 4"×2.5"×1".

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

BRIEF DESCRIPTION OF THE DRAWINGS

This invention is further understood by reference to the drawings wherein.

DETAILED DESCRIPTION OF THE INVENTION

The present invention provides methods and systems (including devices) for assaying analytes in micro- to nanoliter volumes of samples. Specifically, the present invention provides a portable and modular detection system comprising an electromagnetic radiation source, at least one optical element removably attached to an alignment rail, a spatial filter removably attached to the alignment rail, a dichroic mirror, a photodetector, and a lock-in amplifier. In some embodiments, the electromagnetic radiation source, the alignment rail, the optical element removably attached to the alignment rail, the photodetector, and the lock-in amplifier are contained in a housing. In some embodiments, the electromagnetic radiation source, the alignment rail, the optical element removably attached to the alignment rail, the photo detector, and the lock-in amplifier are operably linked to each other. As used herein, "operably linked" refers to two or more components of the modular detection system which are arranged to function together. For example the electromagnetic radiation source is operably linked with a second, dichroic mirror by a first mirror which directs the electromagnetic radiation from the electromagnetic radiation source to the second dichroic mirror.

The present invention also provides methods for assaying an analyte comprising
collecting and collimating any reflected or emitted electromagnetic radiation from the analyte with at least one optical element removably attached to at least one alignment rail,
directing the collimated electromagnetic radiation to a photodetector,
converting the reflected or emitted electromagnetic radiation to a voltage signal,
using phase sensitive detection to provide an amplified voltage signal, and obtaining the amplified signal within a housing capable of being portable.

Figure 1A:
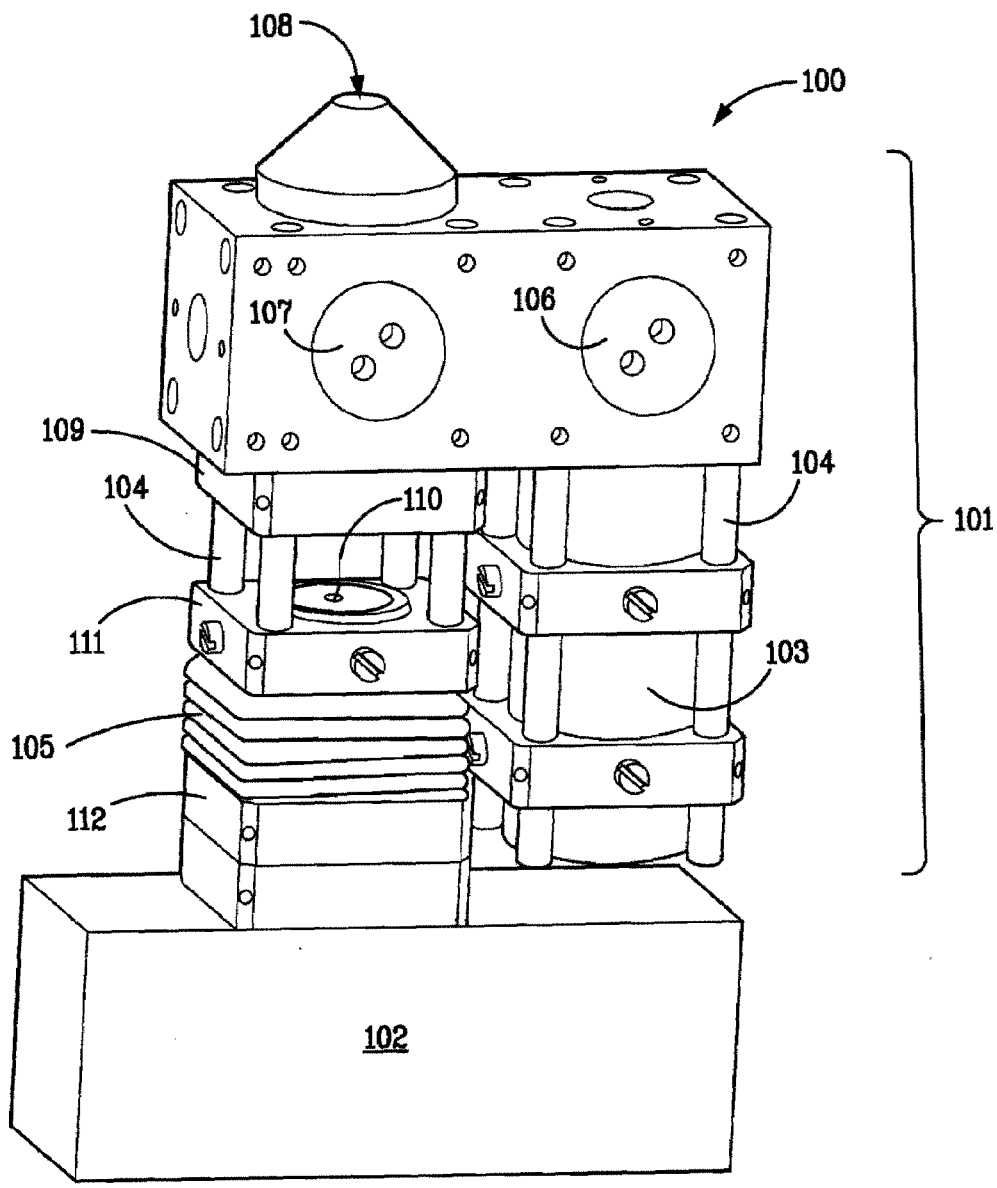
FIG. 1A is a schematic showing an exterior view of an embodiment of the present invention.

FIG. 1A is a schematic of the exterior of a detection system 100 according to the present invention. As shown, the detection system 100 is about 3"× about 2.125"× about 0.75" in size. The dimensions of the detection system of the present invention may vary in size, ranging from an average bench mounted device to a palm sized device. In some embodiments, the detection system of the present invention is portable, preferably capable of being handheld.

The detection system of the present invention may be used to assay electromagnetic radiation ranging the span of the electromagnetic spectrum, preferably from about 10 nm (ultraviolet spectrum) to about 1 mm (infrared spectrum), more preferably about 256 nm to about 1064 nm (visible spectrum) reflected or emitted from analytes in samples. In some embodiments, fluorescence emitted from analytes or fluorophores attached to analytes of interest in samples is assayed. In these embodiments, the fluorophore may be any one of many known in the art or commercially available and readily selected and utilized by those skilled in the art.

As used herein, an "analyte" refers to a particle that may be natural or synthetic and includes natural or synthetic compounds and biomolecules, such as polymers, environmental pollutants, pesticides, insecticides, drugs such as cocaine and antibiotics, magnetic particles, high-magnetic-permeability particles, metal ions, metal ion complexes, inorganic ions, inorganic ion complexes, organometallic compounds, metals including aluminum, arsenic, cadmium, chromium, selenium, cobalt, copper, lead, silver, nickel, and mercury, and the like, amino acids, peptides, proteins, nucleotides, nucleic acids, carbohydrates, lipids, cells, viruses, viral particles, bacteria, organelles, spores, protozoa, yeast, mold, fungi, pollen, diatoms, and the like, and ligands, toxins, biotoxins, hormones, steroids, immunoglobulins, antibodies, supermolecular assemblies, catalytic particles, zeolites, and the like, and biological and chemical warfare agents, agents used in explosives, and the like. In some embodiments, the analytes of interest are labeled with a probe, preferably a fluorophore, which emits a detectable wavelength.

As provided herein, the sample may be a fluid, solid or colloid. In preferred embodiments, the sample is a fluid. As used herein, a "fluid" refers to a continuous amorphous substance that tends to flow and to conform to the outline of a container such as a liquid or a gas. Samples include blood, plasma, urine, bile, breast milk, semen, water, liquid beverages, air, saliva, food, and the like.

The samples may be provided on or in a substrate such as a slide, vial, biochip, a microfluidic device, or the like. As used herein, "microfluidic" refers to a system or device having one or more fluidic channels, conduits or chambers that are generally fabricated at the millimeter to nanometer scale which allow a fluid to pass through. As used herein, "channel" refers to a structure wherein a fluid may flow. A channel may be a capillary, a conduit, a strip of hydrophilic pattern on an otherwise hydrophobic surface wherein aqueous fluids are confined, and the like. Thus, the "microfluidic channels" or alternatively referred to herein as "microchannels" of the present invention generally have cross-sectional dimensions ranging from about 1 mm or less, preferably between about 1,000 µm and about 1 µm, more preferably between about 500 µm and about 1 µm, most preferably between 100 µm and about 5 µm. As used herein, a "microfluidic channel" is intended to mean one or more channel segments which are in fluidic communication, i.e. a fluid may pass there between. Thus, a second channel segment may be oriented at an angle to a first channel segment, but because the two segments are in fluidic communication, the channel segments are considered to be a "microfluidic channel".

As provided herein, the methods and systems of the present invention utilize at least one optical element removably attached to at least one alignment rail, thereby making the detection system modular. As used herein, an "optical element" refers to a lens, mirror, dichroic mirror, interference filter, color filter, pinhole, aperture, iris, diffractive element, prism, polarizer, wave plate, collection optic and the like. As exemplified herein, a flat mirror was used in conjunction with a dichroic mirror, a lens, and a spatial filter having two lens elements, a pinhole, and an interference filter. However, those skilled in the art may readily select the optical element(s) used in accordance with the present invention for a desired application. In some embodiments, the optical elements are known in the art or commercially available.

As used herein, an "alignment rail" refers to an elongated linear structure. The alignment rail may be any desired shape so long as the dimensions radially outward from a center axis remain constant to allow translation of the modular components along the length of the alignment rail. If the radius changes, the rail surface could, for example, take the form of a wave. For the modules to be positioned with accuracy, the rail to module interface must be a very close tolerance. Translate simply means to move the element up or down on the rail. In some embodiments, the alignment rail is a rod having a cross-sectional shape that may be any desired shape, preferably round, square, triangular, elliptical, and the like. In preferred embodiments, the alignment rail is a rod with a round cross-sectional shape to allow a component attached thereto to be rotated around the alignment rail.

An optical element may be removably attached to an alignment rail by a variety of methods and means known in the art. For example, an optical element or a holder containing the optical element may be slidable on the alignment rail and secured by fastening with a screw, spring, plunger, friction device, magnet, o-ring, or the like. In some embodiments, the alignment rail contains threads or notches which enable the precise positioning of an optical element at a desired position on the alignment rail. For example, a holder for a given optical element and the alignment rail may have threads such that the holder may be rotated to position the holder at a desired location on the alignment rail. In some embodiments, an optical element may be positioned out of the way to prevent its use during a given application.

In some embodiments, the detection system of the present invention includes at least one collection optic or a collection means that focuses electromagnetic radiation on a sample and collects the emitted or reflected electromagnetic radiation. A collection optic includes lenses (objective or optical), optical fibers, diffractive optics, and the like, and means known in the art for collecting the electromagnetic radiation reflected or emitted from the analytes or labels in the sample. Such collection optics are known in the art or commercially available. See, for example, 5721-A-H Aspheric lens, available from New Focus (San Jose, Calif.). In some embodiments, the collection optics are removably attached to the alignment rail, thereby allowing one to select and implement a desired numerical aperture, magnification, anti-reflection coating, and the like.

In some embodiments, the detection system of the present invention may include a filter, such as dichroic filter, color filter, interference filter, diffraction filter, prism, and the like to filter the collected electromagnetic radiation reflected or emitted from the analytes or their labels. Such filters are known in the art or commercially available. See, for example, 633NB3 laser line filter, 640DRLP dichroic filter, and a 670DF40 emission filter available from Omega Optical (Brattleboro, Vt.). The filters may be removably attached to the alignment rail, thereby allowing one to select and implement a filter for a particular application. Those skilled in the art may readily select a filter or filter combination using methods known in the art.

In some embodiments, where an optical element is contained in a holder that is removably attached to an alignment rail, the optical element may be removably attached to its holder by methods known in the art. In some embodiments, the position of the optical element may be modified within its holder by methods known in the art. For example, the angle, rotation, and absolute position with respect to the optical axis of the optical element may be readily modified.

The detection systems of the present invention may include an electromagnetic radiation source such as a laser, a low power laser such as a laser diode, diode based lasers (lasers pumped by diode, frequency doubled or tripled laser diodes), a light emitting diode (LED), vertical cavity surface emitting lasers (VCSELs), vertical external cavity surface emitting lasers (VECSELs), dipole pumped solid state (DPSS) lasers, and the like or fiber optic connections that can be subsequently coupled to light sources such as large laser systems, laser diodes or lamps. In some embodiments, the laser is a pulsed laser. Such electromagnetic radiation sources are known in the art and commercially available. See, for example, VLM2 635 nm 4 mW diode laser available from Coherent Inc. (Santa Clara, Calif.).

In some embodiments, the electromagnetic radiation source is removably attached to at least one alignment rail, which may be the same or different from the alignment rail to which the optical elements are removably attached. The ability to readily remove a given electromagnetic radiation source and replace it with another electromagnetic radiation source allows one to use the detection system of the present invention with various assay formats. For example, a laser may be used to excite a fluorophore attached to an analyte in a sample and detection of fluorescence emitted from the fluorophore indicates the presence of the analyte. Then the laser may be replaced with a different light source or a laser having a different wavelength in order to detect a different fluorophore in the same sample or a different sample.

The detection system of the present invention may further include a filter for filtering the electromagnetic radiation from the electromagnetic radiation source such as a laser line filter and the like. Such filters are known in the art or commercially available. See, for example, laser line filter 633NB3 available from Omega Optical (Brattleboro, Vt.). In some embodiments, the filters may be removably attached to the detection system in accordance with the present invention or by methods known in the art.

Those skilled in the art may readily optimize the volume or area of a sample that is subjected to the electromagnetic radiation using methods known in the art, e.g. selection of collection lens numerical aperture, magnification, depth of focus, and the like. Such lenses are known in the art or commercially available. See, for example, 5721-A-H Aspheric lens, available from New Focus (San Jose, Calif.).

The detection systems of the present invention may include a photodetector, such as photoresistors, photovoltaic cells, photodiodes, photomultiplier tubes, phototubes, phototransistors, a charge-coupled device (CCD), and the like. In some embodiments, the photodetector is a photomultiplier tube (PMT) or a photodiode. The photodetector may be removably attached in accordance with the present invention or by methods known in the art.

In some embodiments, the detection system of the present invention includes an amplifier or a means for increasing the signal-to-noise ratio of the signals generated by the photodetector such as low noise voltage preamplifiers and the like. Such preamplifiers are known in the art or commercially available. See, for example, SRS 560 Low Noise Preamplifier available from Stanford Research Systems (Sunnyvale, Calif.). In preferred embodiments, the signal-to-noise ratio is increased with a lock-in amplifier. In preferred embodiments, the lock-in amplifier is contained within the housing of the detection system, for example, the detector module of the system.

Figure 2:
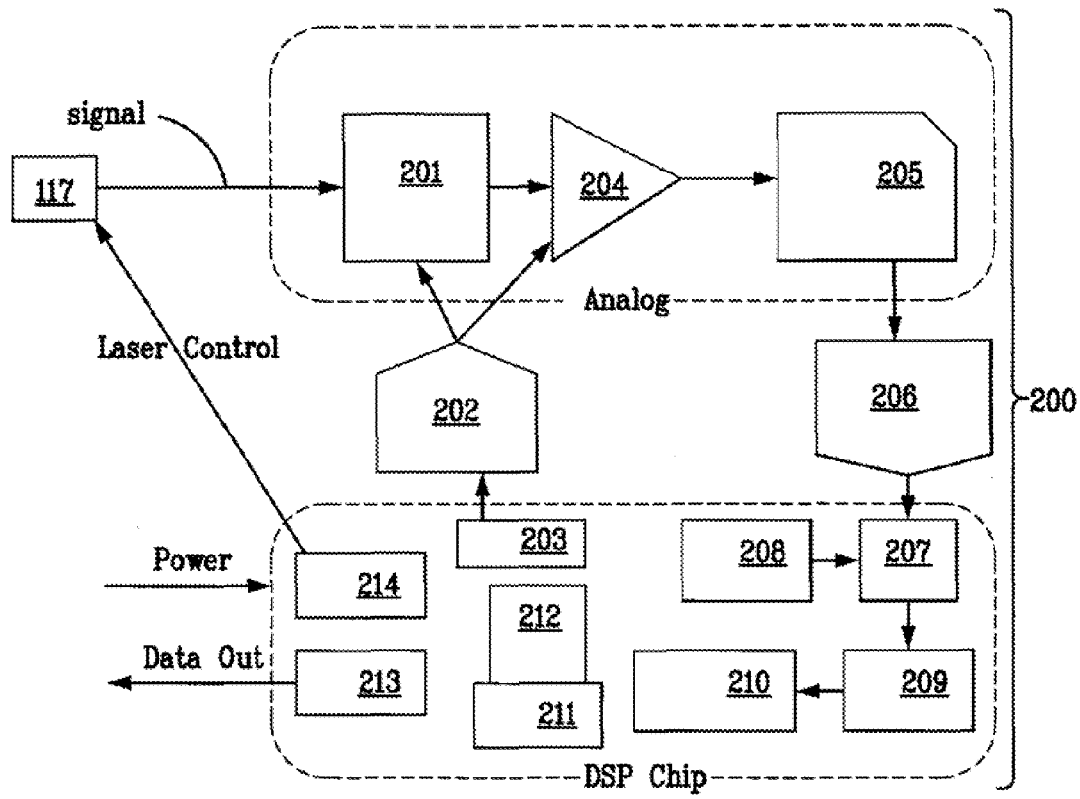
FIG. 2 is a schematic of a lock-in amplifier according to the present invention.

FIG. 2 shows a schematic of a lock-in amplifier 200 according to the present invention. In some embodiments, the lock-in amplifier is reprogrammable such that the reference frequency may be selected, modulated or changed. The modulation of the excitation source and reference frequency can be set to a range that falls within the experimental parameters. This allows the user to put the lock-in frequency in an ideal range for a given application and the noise conditions that exist in a particular environment. While prior art lock-in amplifiers are confined to the laboratory bench in the form of a 19" rack-mounted unit, the lock-in amplifier of the present invention is preferably in the form of a small (about 2"× about 1.5") circuit board. The lock-in amplifier of the present invention is based on a fast digital signal processor (DSP) integrated circuit 220 that can implement the lock-in detection and post filtering in a reprogrammable chip. The lock-in amplifier also includes analog circuitry 230 to pre-filter the signal and adjust the amplifier gain and offset. The lock-in amplifier internally generates the chopping waveform applied to the sensor excitation. This internal chopping waveform eliminates the need for an external mechanical chopper wheel. Preferably, the lock-in amplifier of the present invention provides lock-in detection and post filtering on a single integrated circuit.

As provided in FIG. 2, the lock-in amplifier 200 comprises a digital potentiometer 202, an amplifier 204, an anti-aliasing filter 205 (a 10th order elliptical filter), an analog to digital converter 206, and a DSP chip which comprises elements 203 and 207-214. The components for a lock-in amplifier 200 according to the present invention are known in the art or commercially available. For example, AD5235 available from Analog Devices, Inc. (Costa Mesa, Calif.) may be used as the digital potentiometer 202, LT6234 and LTC1569-6 available from Linear Technology (Milpitas, Calif.) may be used as the amplifier 204 and the anti-aliasing filter 205, respectively, and ADS8327 and TMS320F2808 available from Texas Instruments (Dallas, Tex.) may be used as the analog to digital converter 206 and the DSP chip (comprising elements 203, 207-214), respectively. It is noted, however, that other chips known in the art may be readily selected and implemented by those skilled in the art to optimize speed, reduce noise and provide a desired level of lock-in performance.

As provided in FIG. 2, a voltage signal from a photo detector is transformed by a DC voltage offset 201 and analog gain amplifier 204. The DSP chip digitally controls this offset and gain through a programmed serial peripheral interface (SPI) 203 to a digital potentiometer 202. Then anti-aliasing filter 205 attenuates frequencies above about 2 kHz in order to prevent aliasing in the analog to digital (A/D) converter 206. The A/D converter 206 samples the analog signal with 16 bit resolution at 10 kHz and transfers the digital signal to the DSP chip through SPI 203. The following functions, 207-214, are all implemented digitally in programmed C and Assembly code downloaded to the DSP chip. A CPU timer interrupt 208 calls the SPI routine 207 to sample the A/D converter 206 every 10 kHz. The data is placed in an array and demodulated 209 with sine and cosine waveforms at the 220 Hz laser modulation frequency. The result of this calculation is sent though a 2000th order FIR low pass filter 210 to yield the final digital output signal, which is then transferred to a data collector, a data memory or a data display through an Inter-Integrated Circuit ($I^2C$) Protocol 213. The DSP chip also controls pulsing a laser at 220 Hz through an internal timer 214 toggling a GPIO pin. Also shown in the diagram are a main code section 212, representing the program flow, and a memory section 211, representing the data and program sections stored in the DSP chip memory. It should be noted that, those skilled in the art may readily adapt the DSP chip for a given application by modifying its software programming using methods known in the art.

In some embodiments, the detection system further comprises a spatial filter. By carefully selecting lenses and a pinhole, a specific volume element in the sample may be analyzed. As exemplified herein, the spatial filer uses a 10.8 mm focal length lens that focused the collected electromagnetic, i.e. fluorescence, signal and passes it through a 500 μm pinhole. The light is then re-collimated using a matching 10.8 mm focal length lens. Both lenses are anti-reflection coated for the wavelengths used. The spatial filter effectively blocks off axis light (scatter) that in its absence would have a free path to the photodetector. The fully customizable spatial filter on the emission allows the user to interchange pinhole diameters to further refine the area of interest, as well as, the free selection of lens combinations to focus the electromagnetic radiation, i.e. light, through the pinhole and re-collimate it onto the detector face. In some configurations, the second lens in the filter can be omitted. In some embodiments, the spatial filter may be substituted or combined with a filter comprising a single lens, a pinhole filter, light baffling, or a combination thereof which are known in the art.

In some embodiments, the detection system further comprises light baffling or means for preventing or blocking undesired light from entering the detection system. Examples of light baffling include pinholes, threading walls in light path, annular rings, and the like. Such light baffling and means are known in the art or commercially available. See, for example, iris diaphragms available from Newport Corporation (Irvine, Calif.). The light baffling may be removably attached to the alignment rail. Those skilled in the art may readily position the light baffling at desired locations in the light path to accommodate different lens combinations and scatter profiles using methods known in the art.

In some embodiments, the detection system comprises a display or means for displaying the results of analysis. Examples include a liquid crystal display (LCD), oscilloscope, strip chart reader, voltmeter, and the like. Such displays and means are known in the art or commercially available.

In some embodiments, the detection system comprises data memory storage or means for storing the results of analysis. Such data memory storage and means are known in the art or commercially available.

In some embodiments, the detection system comprises a data output connector or means for exporting the results of analysis to an external data processor, such as a computer or the like. Examples include a 10 pin connector or receptacle thereof, serial interface, USB interface, cable, ribbon, and the like. Such data output connectors and means are known in the art or commercially available.

In some embodiments, the detection system of the present invention may include a voltage source for operation of the electromagnetic radiation source, photodetector, lock-in amplifier, or a combination thereof. In some embodiments, the detection system of the present invention includes a voltage input or means for providing electricity for operation of the electromagnetic radiation source, photodetector, lock-in amplifier, or a combination thereof. Suitable voltage sources and inputs are known in the art or commercially available.

As provided in FIG. 1A, the detection system 100 may be characterized as having two sections, an optics section 101 and a detector section 102. The optics section 101 contains an electromagnetic radiation source 103, e.g. a light source, and optical elements for generating, collimating, shaping the electromagnetic radiation (e.g. light) beam, directing the resulting beam onto a photo detector contained in the detector section 102. At least one optical element is removably attached to at least one alignment rail 104. The optics section may comprise light baffling 105 which prevent undesired electromagnetic radiation from entering the detection system 100. Alternatively, the optics section 101 may be contained in a covering to prevent undesired electromagnetic radiation from entering the detection system 100. The light baffles 105 may be removably attached to the optics section, e.g. to the alignment rail 104. An adjuster 106 may be employed to adjust an optical element, such as mirror 113, or the like, which directs a wavelength from the light or excitation source 103 to dichroic mirror 114. A dichroic mirror adjuster 107 may be employed to adjust the deflection of electromagnetic radiation, e.g. light, through a lens 108 onto a sample to be assayed and the passage of electromagnetic radiation emitted from analytes in the sample to a lens contained in a lens holder 109 which focuses the electromagnetic radiation through a pinhole filter 110 contained in a pinhole filter holder 111. Electromagnetic radiation passing through the pinhole filter 110 is directed to a lens in a lens holder 112 which focuses the electromagnetic radiation on a photodetector.

Figure 1B:
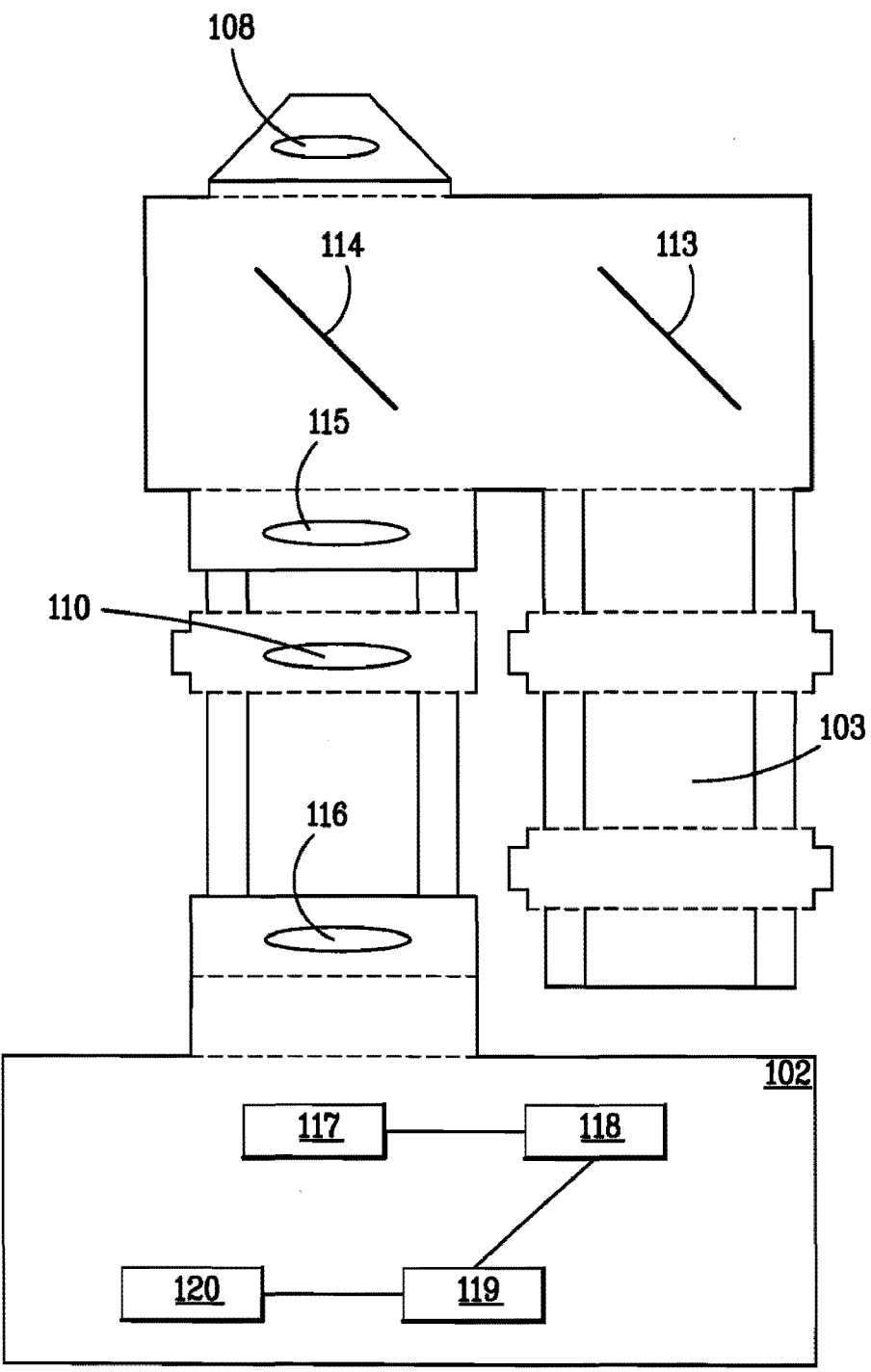
FIG. 1B is a cross-sectional view of FIG. 1A.

As shown in FIG. 1B, mirror 113 directs the electromagnetic radiation from the electromagnetic radiation source 103 to dichroic mirror 114 which then deflects the electromagnetic radiation to lens 108 which focuses the electromagnetic radiation on a sample to be analyzed. The electromagnetic radiation reflected or emitted from the analytes in the sample is then collected and collimated, again by lens 108. The collimated electromagnetic radiation passes through dichroic mirror 114 to lens 115 which focuses the electromagnetic radiation through pinhole filter 110 to lens 116. Lens 116 allows flexibility as the focal length and position of lens 116 may be readily selected by those skilled in the art to focus the electromagnetic radiation at a desired distance such that photo detector 117 may be placed at a desired position.

In the some embodiments, photo detector 117, such as a photomultiplier tube, is an integral part of detector section 102. The detector section 102 includes a transimpedance amplifier 118 that converts the photocurrent signal into a voltage which is digitized with an analog-to-digital converter (ADC) 119 and then amplified with a miniaturized lock-in amplifier 120. The detection system of the present invention may further include an integrated energy source, an integrated memory chip, a data processing chip, and an integrated monitor such as a liquid crystal display (LCD) for displaying the progress or results of the detection system.

The detection system of the present invention may be readily optimized for a desired application by those skilled in the art by selecting the electromagnetic radiation source and optical elements. For example, an additional dichroic mirror may be placed below the spatial filter to direct a desired wavelength of light to an additional detector. This configuration allows for multiple emission wavelengths to be detected.

In practical use, an operator initiates an assay by sending an appropriate signal, for example, by pressing a start button. Operation of the system may be terminated automatically, based on a given time or signal output, or manually.

The detection system of the present invention may further include a stage for positioning the sample or substrate to be analyzed. However, in preferred embodiments, the detection system of the present invention does not have a stage or the stage is removably attached in order to accommodate various substrates such as microchips, capillaries, and microscope slides, and samples that may be assayed.

In some embodiments, the detection system of the present invention is fully self contained detection system, i.e. comprises an excitation (electromagnetic) source, filtering and beam steering optics, and a detector housed together as a single device. In some embodiments, the detection systems of the present invention may be complexed with bench optical systems, liquid chromatography systems, and capillary electrophoresis systems known in the art, and the like, using methods known in the art.

As provided herein, the detection systems of the present invention are superior to prior art portable detection systems. For example, although U.S. Pat. No. 6,998,598 claims picomolar detection limits, the device described therein does not reliably provide low nanomolar and even femtomolar detection limits. The detection system of the '598 patent purports a dovetail design that makes the system modular. Unfortunately, the collection optics sits directly above a fixed mirror and detector and placement of the optics on a dovetail only allows of very small movements such that if one wanted to implement optics of a different design than that provided, the optics would have to be precisely aligned with the detector unit below. In other words, substitute optics would have to be in the exact same position as the replaced optics for the unit to operate. Further, the design of the detection system disclosed in the '598 patent does not allow the implementation of additional optical elements such as a spatial filter.

Further, in the detection system disclosed in the '598 patent, the upper unit is designed to hold one microfluidic chip. In order to focus the laser excitation on the chip (the Z direction), one must raise and lower the optics in the module. This movement of the lens changes the collection light path and this can take it off the collection face of the PMT. Specifically. by moving the lens to focus on the microchip, the pack focus point may change and cause some of the collected light to miss the active area on the PMT. Additionally, to line up the excitation source with a given area on the microfluidic chip, one must translate the lens back and forth (the X direction). This movement ultimately moves the collected light out of co-linearity with the collection path.

In addition, in the detection system disclosed in the '598 patent, the steering mirrors used to extend the optical path length are problematic. First, the mounts that hold the mirrors must be machined perfectly to keep the beam from gradually walking up or down out of the preferred light path. In other words, if the parts have a slight tilt up, the beam will diverge from the centerline and tend to exit the optical path, thereby making maintaining co-linearity challenging and timely.

As provided herein, unlike the design of the '598 patent, the detection system of the present invention is truly modular in that its components are readily interchangeable, swappable, moveable, and replaceable while maintaining co-linearity.

Although the device and design disclosed in U.S. Pat. No. 6,407,395 ('395 patent) appears to, on a cursory review, be similar to the detection system of the present invention, it is not. Specifically, the '395 patent employs a light source working in continuous-wave mode which means that the light is always on (e.g. a DC signal). Use of a DC signal requires use of a simple filter design and nothing else. In other words, since the '395 patent does not use a modulating light source, it can not implement lock-in amplification as does the present invention.

Further, the design disclosed in the '395 patent is not modular. In particular, there is no disclosure indicating that the optical elements and laser are removably attached and that such may be substituted or their positions changed along an alignment rail. Thus, the device disclosed in the '395 patent can not be readily modified for given applications and assay formats.

As provided herein, the modularity of the detection system of the present invention is the ability to replace various elements, including optical elements, without requiring extensive realignment or recalibration of the components. The modular concept provides for the use of a wide variety of components to fit particular needs. For example, almost any electromagnetic radiation source can be used in the system such as light-emitting diodes, laser diodes, vertical cavity surface emitting VCSELs, VECSELs, DPSS lasers or fiber optic connections that are subsequently coupled to light sources such as large laser systems, laser diodes or lamps. Optical elements can include lenses and filters either singly or in combination, that are totally interchangeable to accommodate the light source. Filters can be implemented to filter out background radiation. More complex optical elements such as blazed or holographic gratings can be included to condition the excitation and emission radiation in ways that cannot be accomplished by filters alone. As provided herein, the photodetector used may be readily selected from one of many known in the art, including photomultiplier tubes, photodiodes, avalanche photodiodes, photodiode arrays, charge-coupled devices, and photosensitive detectors, for a desired application.

As provided herein, laboratory measurements using the detection system containing a lock-in amplifier in accordance with the present invention provides a large improvement in both the signal-to-noise and the signal-to-offset (due to rejection of the background electromagnetic radiation) over prior art devices.

Figure 3:
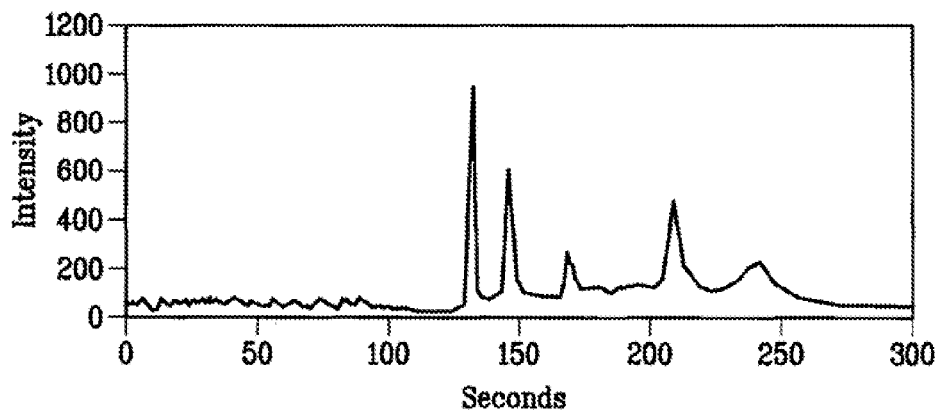
FIG. 3 is a graph which shows the detection of double-stranded RNA after separation by gel electrophoresis.

FIG. 3 is a graph which shows the detection of double-stranded RNA after separation by gel electrophoresis. The specific conditions were: 25 ng/µl RNA (Invitrogen, San Diego, Calif.) labeled with 1/6 Agilent bioanalyzer dye (RNA 6000 NANO LABCHIP® Kit, Agilent Technologies, Palo Alto, Calif.) in 1× Native tris-gly pH 8.9 (BioRad, Hercules, Calif.) was injected at 150 V/cm and separated at 333 V/cm. The RNA was separated using a standard T-chip (Caliper Life Sciences, Hopkinton, Mass.). A polyacrylamide gel was fabricated at about a 3.5% acrylamide (Sigma-Aldrich, St. Louis, Mo.) concentration within the T-chip for polyacrylamide gel electrophoresis to separate the RNA.

Figure 4:
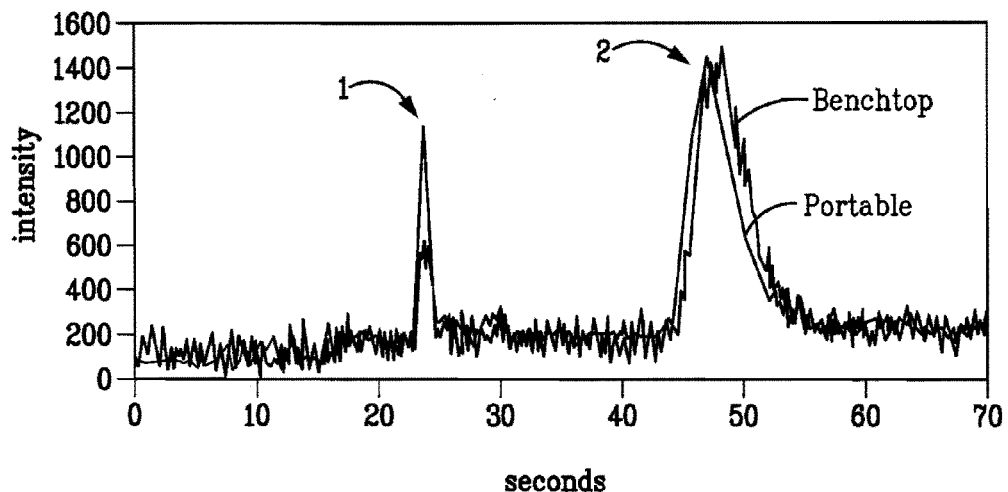
FIG. 4 graphically compares the detection with a system according to the present invention with that of a standard benchtop epifluorescent system without the use of lock-in amplification.

FIG. 4 graphically compares the detection with a detection system according to the present invention with that of a conventional benchtop epifluorescent system without the use of lock-in amplification known in the art. 50 nm Anti-MMP8 (United States Biological, Swampscott, Mass.) labeled with ALEXA FLUOR® 647 dye (invitrogen, San Diego, Calif.) in 1× Native tris-gly pH 8.9 (BioRad, Hercules, Calif.), was injected at 150 V/cm and separated at 333 V/cm. The protein was separated using a standard T-chip (Caliper Life Sciences, Hopkinton, Mass.). A polyacrylamide gel was fabricated at about a 6% acrylamide (Sigma-Aldrich, St. Louis, Mo.) concentration within the T-chip for polyacrylamide gel electrophoresis to separate the protein. Peak 1 represents unbound ALEXA FLUOR® 647 dye, Peak 2 represents anti-MMP8. Signal/Noise: portable=peak 1, 61.8/1; peak 2, 75.9/1. Benchtop=peak 1, 10/1; peak 2, 26.8/1.

Figure 5:
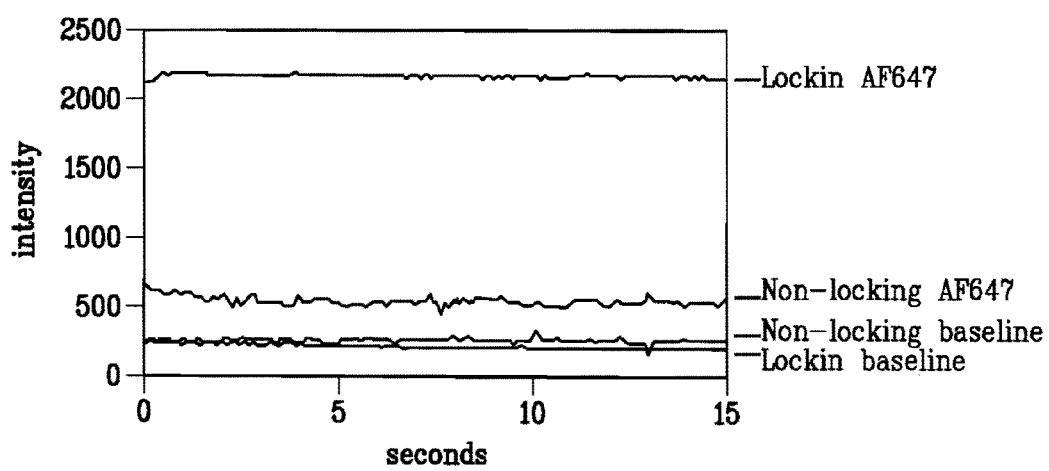
FIG. 5 graphically compares detection with a system according to the present invention without a lock-in amplifier with one having a lock-in amplifier at 500 volt PMT setting, gain at 100×.

FIG. 5 graphically compares detection with a detection system according to the present invention without a lock-in amplifier with one having a lock-in amplifier at 500 volt PMT setting, gain at 100×. Signal/Noise: no lock-in=19/1; lock-in=192/1. Experiments were done using a standard T-chip (Caliper Life Sciences, Hopkinton, Mass.). The channels of the T-chip were filled with buffer, 1× Native tris-gly (BioRad, Hercules, Calif.) containing no fluorescent dye to obtain baseline measurements for the detection system at 500V both with and without lock-in. Then the T-chip was filled with a buffer containing $2\times10^{-7}$ M ALEXA FLUOR® 647 dye (Invitrogen, San Diego, Calif.) to obtain comparison data to the baseline.

Figure 6:
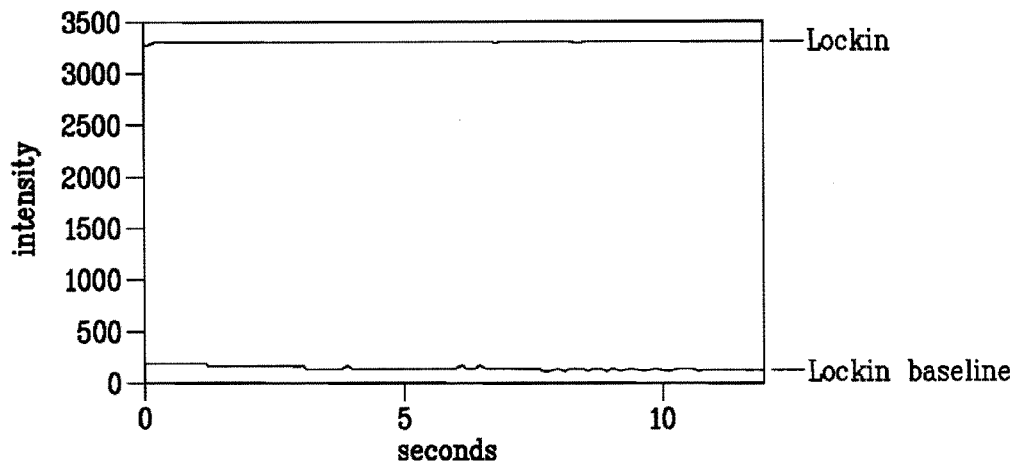
FIG. 6 shows detection with a system according to the present invention with a lock-in amplifier at 700 volt PMT setting, gain at 100×.

FIG. 6 shows detection with a detection system according to the present invention with a lock-in amplifier at a 700 volt PMT setting, gain at 100×. Signal/Noise: 175/1. Experiments were done using a standard T-chip (Caliper Life Sciences, Hopkinton, Mass.). The channels of the T-chip were filled with a buffer, 1× Native tris-gly (BioRad, Hercules, Calif.) containing no fluorescent dye to obtain baseline measurements for the system at 700V both with and without lock-in. Then the T-chip was filled with a buffer containing $2\times10^{-7}$ M ALEXA FLUOR® 647 dye (Invitrogen, San Diego, Calif.) to obtain comparison data to the baseline.

Figure 7:
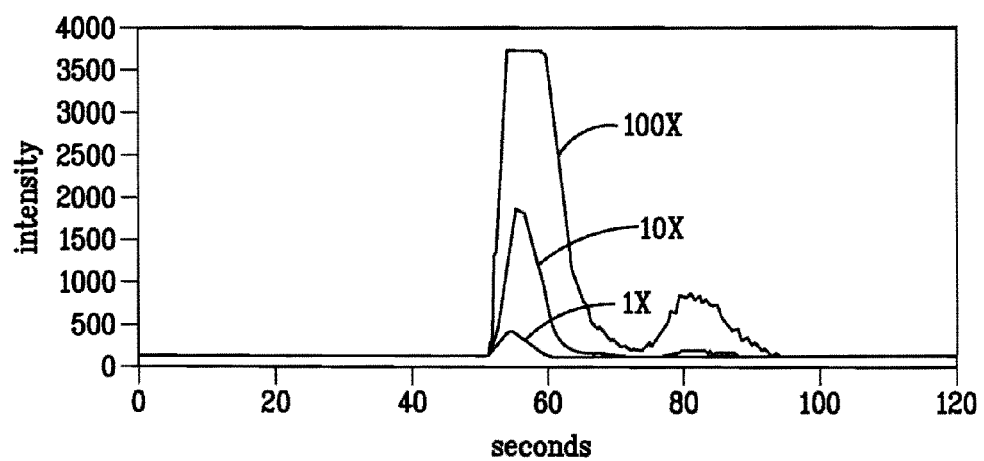
FIG. 7 shows detection with a system according to the present invention at gain settings of 1×, 10×, and 100× with a lock-in amplifier.

FIG. 7 shows detection with a system according to the present invention at gain settings of 1×, 10×, and 100× with a lock-in amplifier. T-chip injections of 2 nM of bovine serum albumin (BSA) (Sigma-Aldrich, St. Louis, Mo.) labeled with ALEXA FLUOR® 647 dye (Invitrogen, San Diego, Calif.) was separated using a standard T-chip (Caliper Life Sciences, Hopkinton, Mass.). The protein was separated using a standard T-chip (Caliper Life Sciences, Hopkinton, Mass.). A polyacrylamide gel was fabricated at about a 6% acrylamide (Sigma-Aldrich, St. Louis, Mo.) concentration within the T-chip for polyacrylamide gel electrophoresis to separate the protein.

Figure 8:
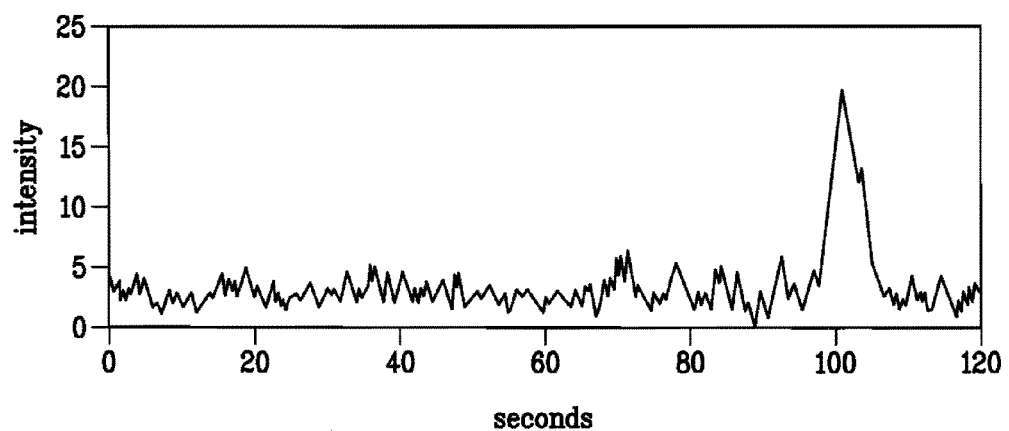
FIG. 8 shows detection with a system according to the present invention with a lock-in amplifier at 750 volt PMT setting, gain at 100×.

FIG. 8 shows detection with a detection system according to the present invention with a lock-in amplifier at a 750 volt PMT setting, gain at 100×. 200 pM of bovine serum albumin (BSA) (Sigma-Aldrich, St. Louis, Mo.) labeled with ALEX FLUOR® 647 dye (Invitrogen, San Diego, Calif.) in 1× Native tris-gly pH 8.9 (BioRad, Hercules, Calif.), was injected at 150 V/cm and separated at 333 V/cm. The protein was separated using a standard T-chip (Caliper Life Sciences, Hopkinton, Mass.). A polyacrylamide gel was fabricated at about a 6% acrylamide (Sigma-Aldrich, St. Louis, Mo.) concentration within the T-chip for polyacrylamide gel electrophoresis to separate the protein. Signal/Noise=21.5/1.

Figure 9:
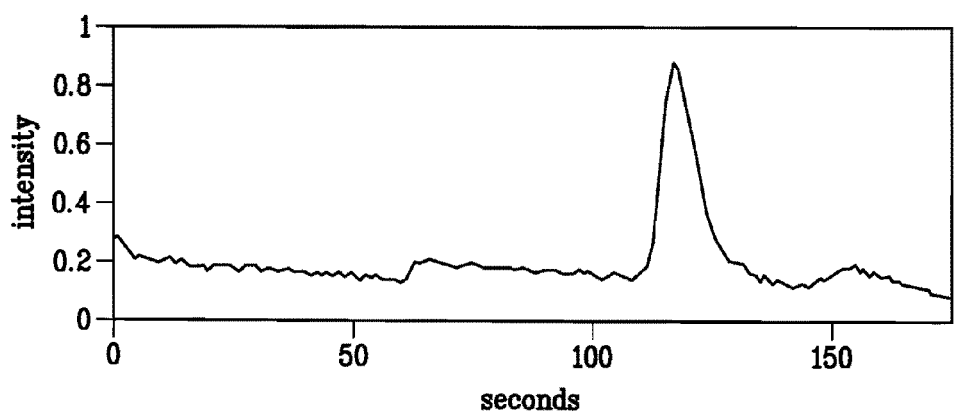
FIG. 9 shows a benchtop laser setup with commercial lock-in amplifier at 750 volt PMT setting.

FIG. 9 shows a benchtop detection system with a commercial lock-in amplifier at a 750 volt PMT setting. 200 pM of bovine serum albumin (BSA) (Sigma-Aldrich, St. Louis, Mo.) labeled with ALEXA FLUOR® 647 dye (Invitrogen, San Diego, Calif.) in 1× Native tris-gly pH 8.9 (BioRad, Hercules, Calif.), was injected at 150 V/cm and separated at 333 V/cm. The protein was separated using a standard T-chip (Caliper Life Sciences, Hopkinton, Mass.). A polyacrylamide gel was fabricated at about a 6% acrylamide (Sigma-Aldrich, St. Louis, Mo.) concentration within the T-chip for polyacrylamide gel electrophoresis to separate the protein. Signal/Noise=117/1.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

We claim:

1. A portable and modular detection system comprising:
   an electromagnetic radiation source;
   at least one alignment rail;
   a plurality of modular optical elements each removably attached along a length of the alignment rail, wherein the plurality of modular optical elements are individually translatable along the length of the alignment rail;
   a dichroic mirror;
   a photo detector; and
   a lock-in amplifier, wherein the dichroic mirror re-directs electromagnetic radiation generated by the electromagnetic radiation source through a collimating lens and onto an analyte sample, wherein the collimating lens collects radiation radiation reflected or emitted by the analyte sample in response to the generated electromagnetic radiation and directs the collected electromagnetic radiation onto the dichroic mirror, wherein the dichroic mirror directs the collected electromagnetic radiation into the plurality of modular optical elements, wherein the plurality of modular optical elements operate to shape, collimate and direct the collected electromagnetic radiation into the photo detector, wherein the photo detector converts the collected electromagnetic radiation into a voltage signal, and wherein the voltage signal is amplified by the lock-in amplifier.

2. The detection system of claim 1, wherein the electromagnetic radiation source produces a wavelength ranging from infrared to ultraviolet.

3. The detection system of claim 1, wherein the electromagnetic radiation source is a laser, a pulsed laser, or a light emitting diode.

4. The detection system of claim 1, wherein the optical element is a lens, a mirror, a dichroic mirror, an interference filter, a color filter, a pinhole, an aperture, an iris, a diffractive element, a prism, a polarizer, a collection optic, or a wave plate.

5. The detection system of claim 1, wherein the photo detector is a photoresistor, a photovoltaic cell, a photodiode, a photomultiplier tube, a phototube, a phototransistor, or a charge-coupled device.

6. The detection system of claim 1, and further comprising a spatial filter which is optionally removably attached to the alignment rail.

7. The detection system of claim 1, and further comprising a light baffling, a stage, a display, a data memory storage, a voltage source, or a combination thereof, which are each independently optionally removably attached.

8. The detection system of claim 1, wherein the photo detector, the electromagnetic radiation source, and the lock-in amplifier are each independently optionally removably attached.

9. The detection system of claim 1, having a size less than about 4"×2.5"×1".

10. The detection system of claim 1, wherein the electromagnetic radiation source, the alignment rail, the optical element removably attached to the alignment rail, the photo detector, and the lock-in amplifier are contained in a housing.

11. The detection system of claim 1, wherein the electromagnetic radiation source, the alignment rail, the optical element removably attached to the alignment rail, the photo detector, and the lock-in amplifier are operably linked to each other.

* * * * *